(12) United States Patent
Luzio et al.

(10) Patent No.: US 6,428,837 B1
(45) Date of Patent: Aug. 6, 2002

(54) DEESTERIFIED PECTINS, PROCESSES FOR PRODUCING SUCH PECTINS, AND STABILIZED ACIDIC LIQUID SYSTEMS COMPRISING THE SAME

(75) Inventors: Gary Luzio; Susan C. Forman, both of Newark, DE (US); Timothy C. Gerrish, Kennett Square, PA (US)

(73) Assignee: CP KELCO APS, New York, NY (US)

( * ) Notice: Subject to any disclaimer, the term of this patent is extended or adjusted under 35 U.S.C. 154(b) by 0 days.

(21) Appl. No.: 09/589,887

(22) Filed: Jun. 9, 2000

(51) Int. Cl.$^7$ .............................. A23L 2/00; A23L 2/02; A23L 1/0524
(52) U.S. Cl. .......................... 426/599; 426/50; 426/51; 426/577; 426/590
(58) Field of Search ........................... 426/50, 51, 577, 426/599, 590

(56) References Cited

U.S. PATENT DOCUMENTS

| | | | |
|---|---|---|---|
| 4,529,613 A | | 7/1985 | Mezzino et al. |
| 5,286,511 A | | 2/1994 | Klavons et al. |
| 5,639,494 A | * | 6/1997 | Grassin et al. ............... 426/50 |
| 5,648,112 A | | 7/1997 | Yang et al. |
| 5,690,975 A | * | 11/1997 | Akahoshi et al. ............. 426/34 |
| 5,707,847 A | | 1/1998 | Christgau et al. |
| 5,780,081 A | * | 7/1998 | Jacobson et al. ............. 426/74 |
| 5,866,190 A | | 2/1999 | Barey |
| 6,221,419 B1 | * | 4/2000 | Gerrish ....................... 426/577 |
| 6,143,346 A | * | 11/2000 | Glahn ........................ 426/577 |

FOREIGN PATENT DOCUMENTS

| | | |
|---|---|---|
| EP | 0664300 | 7/1995 |
| GB | 1474990 | 5/1977 |
| WO | 89/12648 | 12/1989 |
| WO | 91/15517 | 10/1991 |
| WO | 94/25575 | 11/1994 |
| WO | 97/03574 | 2/1997 |

OTHER PUBLICATIONS

English Language Abstract of JP 8–112059.
Kravtchenko et al., Food Macromolecules and colloids; proceedings of a conference, Dijon, Mar. 1994, 349–355, "Colloidal Stability and Sedimentation of Pectin–Stabilized Acid Milk Drinks".
Kravtchenko et al., "Characterization of Industrial High Methoxy Pectins", pp. 27–35.
Parker et al., Effect of the Addition of High Methoxy Pectin on the Rheology and Colloidal Stability of Acid Milk Drinks, pp. 307–312.
Glahn, FIA–Japan, PEG/JK (dai–24a)—Apr. 4, 1995, pp. 1–6, Fig. 1 and pp. 1–4, and pp. 1–4, and pp. 1–3.
Glahn et al., Gums and Stabilisers for the Food Industry 8, edited by Phillips et al,, IIRL PRESS, Properties and Food Uses of Pectin Fractions, pp. 393–402.
Glahn, Prog. Fd. Nutr. Sci., vol. 6, pp. 171–177, 1982,, "Hydrocolloid Stabilization of Protein Suspensions at Low pH".
Speiser et al., Journal of the American Chemical Society, vol. 68 Feb. 1946, pp. 117–133, "Effect of Molecular Association and Charge Distribution of the Gelation of Pectin".
Speiser et al., "Effect of Molecular Weight and Method of Deesterification on the Gelling Behavior of Pectins", 1946, pp. 287–293.
Kohn et al, Die Nahrung, vol. 29, (1985)1, pp. 75–85.
Markovic et al., Experientia (Base1)40(8), 1984, pp. 842–843.
Industrial Gums—Polysaccharides and Their Derivatives, Third Edition, Ed. by Whistler et al, Academic Press, New York, 1993, Chapter 10, pp. 257–291.
Matsuura et al., Agric. Biol. Chem., 51(6), 1675–1677, 1987, "Limit to the Deesterification of Citrus Pectin by Citrus Pectinesterase".
Hill et la., Food Technology, vol. 3, Mar. 1949, pp. 90–93, "Enzyme–Demethylated Pectinates and Their Gelation".
Jarvis, Plant, Cell and Environment (1984) 7, 153–164, "Structure and Properties of Pectin Gels in Plant Cell Walls".
Solms et al., Helv. Chim. Acta, 38, pp. 321–329, "Uber den Mechanismus der enzymatischen Verseifung von Pektinstoffen".
Kohn et al, Collect. Checz. Chem. Commun., 33, pp. 264–269, "Distribution of Free Carboxyl Groups in the Pectin Molecule After Treatment With Pectin Esterase".
Rolin, "Calcium Sensitivity of High Ester Citrus Pectins", Oxford University Press, edited by Glyn O. Phillips et al., pp. 413–422.

* cited by examiner

Primary Examiner—Helen Pratt
(74) Attorney, Agent, or Firm—Greenblum & Bernstein, P.L.C.

(57) ABSTRACT

Enzymatically blocked-deesterified pectins that display pseudoplasticity and substantially no phase separation in aqueous solutions comprising at least one polyvalent cation, and processes for producing the same. Enzymatically blocked-deesterified pectins prepared by deesterifying isolated high methoxyl pectins with enzymes. Processes for suspending particulates using enzymatically blocked-deesterified pectins enzymatically blocked-deesterified pectins prepared by deesterifying isolated high methoxyl pectins with enzymes. Compositions and stabilized aqueous systems containing enzymatically blocked-deesterified pectins prepared by deesterifying isolated high methoxyl pectins with enzymes.

137 Claims, No Drawings

DEESTERIFIED PECTINS, PROCESSES FOR PRODUCING SUCH PECTINS, AND STABILIZED ACIDIC LIQUID SYSTEMS COMPRISING THE SAME

CROSS-REFERENCE TO RELATED APPLICATION

The present application expressly incorporates by reference herein the entire disclosure of U.S. application Ser. No. 09/589,888, entitled "Low Methoxyl Pectins, Processes Thereof, and Stabilized Aqueous Systems Comprising the Same", which is concurrently filed with the present application.

BACKGROUND OF THE INVENTION

1. Field of the Invention

The present invention is directed to enzymatically blocked-deesterified pectins that display pseudoplasticity and substantially no phase separation in an aqueous solution comprising at least one polyvalent cation, and processes for producing the same. In particular, the present invention is directed to enzymatically blocked-deesterified pectins prepared by deesterifying isolated high methoxyl pectins with enzymes. The present invention is also directed to processes for suspending particulates using enzymatically blocked-deesterified pectins prepared by deesterifying isolated high methoxyl pectins with enzymes. Furthermore, the present invention relates to stabilized aqueous systems containing enzymatically blocked-deesterified pectins prepared by deesterifying isolated high methoxyl pectins with enzymes.

2. Background of the Invention and Related Art

The problem encountered with drinks containing insoluble components, such as pulps, essential oils, and the like, is the tendency of the insoluble components to separate, e.g., via sedimentation or creaming.

In order to maintain insoluble components in suspension, xanthan has been added to fruity drinks to raise the viscosity or alter the rheology of the drink. Xanthan, when added to aqueous solutions even at low concentrations, exhibits very strong pseudoplasticity and viscoplasticity at low concentration without any evidence of thixotropy. However, xanthan adds negative organoleptic perception (undesirable mouth-feel) in beverages. Thus, there is a need to provide a suspension aid that has the desired properties of xanthan without the undesired mouth-feel.

Alginates and pectins have been used in beverages to raise viscosity since they do not add negative mouth feel. Alginates and pectins useful for this application, however, tend to undergo syneresis during long term storage. Attempts have been made to use pectins as suspension aids with reduced syneresis properties, but without success.

Pectin is a structural polysaccharide commonly found in the form of protopectin in plant cells. The backbone of pectin comprises -1-4 linked galacturonic acid residues which are interrupted with a small number of 1,2 linked -L-rhamnose units. Some of the carboxyl groups of the galacturonic residues are esterified, typically by methyl groups. The remaining residues are present as free carboxyl groups. Esterification of the carboxyl groups occurs in the plant tissue after polymerization of the galacturonic acid residues. However, it is extremely rare for all of the carboxyl groups to be esterified. Usually, the degree of esterification varies from 0 to 90% of the available carboxylic groups.

The term "degree of esterification" is intended to mean the extent to which free carboxylic acid groups contained in the polygalacturonic acid chain of the pectin have been esterified (e.g., by methylation) or in other ways rendered non-acidic (e.g., by amidation).

Pectin is available as either low methoxyl pectin (LMP) or high methoxyl pectin (HMP). Low methoxyl pectin as defined here has a degree of esterification (DE) of less than about 45% and is highly reactive with cations such as calcium. High methoxyl pectin as defined here has a DE of greater than about 45% and typically is less reactive with polyvalent cations such as calcium.

The structure of the pectin, in particular the degree of esterification, dictates many of its physical and/or chemical properties. For example, pectin gelation caused by the presence of calcium cations depends especially on the degree of esterification. Gelation is believed to result from the calcium ions forming cross-linked complexes with free carboxyl groups of a number of pectin chains causing the formation of a continuous three-dimensional gelled matrix.

Pectin, as first extracted, has a relatively high degree of esterification of about 70–75%. Such pectin is ideal for use in jam and jellies. However, other uses require the preparation of pectins with different setting characteristics. This can be accomplished by modifying pectin to reduce the degree of esterification. One common process for achieving this is an acid hydrolysis. Alternative processes are directed to the use of alkali at low temperatures, ammonia, or to use a pectin methyl esterase.

During deesterification, the ester groups on the pectin can be removed in a random or blockwise manner. When the ester groups are removed from any galacturonic acid residues on more than one of the pectin chains non-sequentially, they are referred to as being deesterified in a "random manner." When the ester groups are removed either at non-reducing ends or next to free carboxyl groups by a single-chain mechanism in a sequential manner, they are referred to as being deesterified in a "blockwise manner," as blocks of unesterified galacturonic acid units are created. The sequential or blockwise removal esters are typically mediated by pectin methyl esterases. The unesterified galacturonic acid units formed by blockwise deesterification are highly reactive to polyvalent cations such as calcium. Pectins having such blocks of unesterified galacturonic acid are said to be "calcium sensitive."

It is well known that the methyl content of pectin is modified in nature by plant pectin esterases that are present in the plant tissue. Many of these plant esterases, usually called pectin methyl esterases (PMEs), demethylate esterified carboxylic groups that are next to at least two contiguous free carboxylic acid groups. The demethylation proceeds in this way forming blocks. For example, the unpurified proteases papain and bromelain from plant tissue are also known to contain pectin methyl esterases as contaminants that demethylate pectins in a blockwise manner.

To a small extent these blocks of unesterified galacturonic acid units occur naturally in commercial high DE pectins when first isolated. In a commercial, pectin having a typical degree of esterification of approximately 68–74%, the length of the free carboxylic blocks may vary from molecule to molecule, and each pectin molecule typically includes several blocks of different lengths. For example, it is known that the distribution of the free carboxyl groups along the polymer chain is important for determining whether the pectin is suitable for use as a stabilizer for acidified milk drinks. It has been proposed that pectin can stabilize a suspension of casein particles by adsorbing onto the surface of the casein particles at specific points of the pectin molecule where the block-deesterified regions occur. To obtain complete stability a significant proportion of the surface of a casein particle should be covered by the pectin. Nevertheless, aside from stabilizing casein these pectins have found limited utility for stabilization of pulp or other materials in typical beverage applications.

Pectins that have been randomly deesterified have also been tested for use in stabilization of particles in liquid foods and beverages. Commercial pectins that have been reduced randomly to low-methoxyl pectins can also be reactive with polyvalent cations such as calcium. Calcium is the most common source of polyvalent cations for food gel applications involving these types of pectins. Gelation is due to the formations of intermolecular junction zones between homogalacturonic acid units. Because of the electrostatic nature of the bonds, pectin gels are very sensitive to conditions that can modify the environment of the carboxyl groups through which the calcium ion is linked to a neighboring pectin molecule. The gel forming ability of pectin increases with decreasing DE, and low methoxyl pectins with a large number of free carboxyl groups are very sensitive to low calcium levels. As the number of free carboxyl groups along the pectin backbone the increasing sensitivity of low DE pectin to calcium is an increased tendency for the pectin to gel and to display syneresis. The properties of gel contraction and syneresis in these types of randomly deesterified pectins are unsuitable for stabilization of particles in liquid foods and beverages.

Other, attempts have been made in the industry to use pectin as a suspending aid. For example, U.S. Pat. No. 5,866,190 issued to Barey discloses compositions for stabilizing a non-milk drink containing insoluble components comprising a pectin and alginate. The pectin of Barey can be amidated or non-amidated HMPs and LMPs. These compositions however display syneresis that is undesirable for this application. It is also essential that the pectin/alginate mixture be dissolved in an aqueous medium in the absence of free calcium ions or that a calcium complexing agent be used. The complexing agent is added either to the pectin/alginate solution or to the fruit juice.

WO 97/03574 from Christensen relates to a process for stabilizing proteins in an acidic environment with a high-ester pectin prepared by a recombinant DNA technique. The high-ester pectin of Christensen has a degree of esterification of about 70 to 80%. However, the high-ester pectin of Christensen is not pseudoplastic in aqueous solution at low concentrations and is of limited value as a suspension aid.

In view of the above, there is an existing need for a pectin suspension aid that has shear thinning behavior for use in aqueous food, cosmetic, and pharmaceutical products.

There is also an existing need for a pectin to produce a stable aqueous system with shear thinning behavior (pseudoplasticity) and acceptable mouth-feel for use as a particle suspending aid. Pseudoplasticity is a Theological behavior most desired for stabilization of particles in aqueous solution. An aqueous solution is characterized as being pseudoplastic if it displays decreasing viscosity with increasing shear rate. A "stable aqueous system" refers to an aqueous system that can maintain stable viscosity without the formation of gels or without phase separation and syneresis. "Stable viscosity" or "stability" refers to the maintenance of the insoluble components in suspension and the homogeneity of the suspension initially formed. Rheologically, the pseudoplasticity of the aqueous system is stable for a time period of at least one to twelve months or longer.

In addition, there is also an existing need for a pectin that does not undergo syneresis upon storage or form a separate gel phase even in the presence of relatively high levels of calcium such as 500 mM.

SUMMARY OF THE INVENTION

In view of the foregoing, one aspect of the invention is directed to enzymatically blocked-deesterified pectins that display pseudoplasticity and substantially no gel-contraction in aqueous solutions comprising at least one polyvalent cation, and processes for producing the same. In particular, the present invention is directed to enzymatically blocked-deesterified pectins prepared by deesterifying isolated high methoxyl pectins with enzymes.

The enzymatically blocked-deesterified pectin of the present invention preferably has a degree of esterification from about 45 to 65%, and more preferably from about 55 to 59%.

The enzymatically blocked-deesterified pectin of the present invention preferably has a calcium sensitivity greater than about 200 cP or a calcium fraction greater than 20, and a Δ degree of esterification from about 5 to 25%, and more preferably from about 8 to 15%.

The enzymatically blocked-deesterified pectin of the present invention is preferably prepared by treating isolated high methoxyl pectin with enzyme. The enzyme is extracted from plant tissues selected from at least one of apples, apricots, avocados, bananas, berries, limes, grapefruits, mandarins, cherries, currants, grapes, mangos, papayas, passion fruits, peaches, pears, plums, beans, carrots, cauliflowers, cucumbers, leeks, onions, peas, potatoes, radishes and tomatoes, preferably papain.

The enzymatically blocked-deesterified pectin preferably has a degree of esterification from about 45 to 65% when the degree of esterification of the isolated high methoxyl pectin is from about 68 to 72%, and more preferably a degree of esterification from about 55 to 59% when the degree of esterification of the isolated high methoxyl pectin is from about 68 to 72%. The isolated high methoxyl pectin preferably has a degree of esterification greater than about 60%, and more preferably greater than about 67%. The isolated high methoxyl pectin is preferably in an aqueous form or powder form.

The isolated high methoxyl pectin is preferably obtained from at least one of citrus peels, apple juices, apple ciders, apple pomade, sugar beets, sunflower heads, vegetables or waste products from plants selected from at least one of apples, sugar beet, sunflower and citrus fruits, and more preferably from at least one of limes, lemons, grapefruits, tangerines and oranges.

The enzymatically blocked-deesterified pectin of is preferably prepared by treating the isolated high methoxyl pectin with an enzyme, wherein the enzyme is extracted from plant tissues selected from at least one of apples, apricots, avocados, bananas, berries, limes, grapefruits, mandarins, cherries, currants, grapes, mangos, papayas, passion fruits, peaches, pears, plums, beans, carrots, cauliflowers, cucumbers, leeks, onions, peas, potatoes, radishes and tomatoes.

In addition, the present invention is also directed to processes for suspending insoluble particles which comprises adding enzymatically blocked-deesterified pectins to acidic liquid system. The enzymatically blocked-deesterified pectin preferably has a calcium sensitivity greater than about 200 cP or a calcium fraction greater than 20, and a Δ degree of esterification from about 5 to 25%.

The process for suspending particles of the present invention further comprises adding calcium ions to the acidic liquid system. The amount of calcium ions is preferably from about 10 ppm to about 2000 ppm, more preferably from about 50 ppm to about 1000 ppm, and most preferably from about 200 ppm to about 600 ppm.

The acidic liquid system can comprise proteins selected from at least one of soy, whey, and casein.

The process for suspending insoluble components of the present invention can further comprise adding a food, cosmetic, or pharmaceutical product to the acidic liquid system.

Furthermore, the present invention relates to stabilized aqueous systems containing (a) at least one enzymatically blocked-deesterified pectin that displays pseudoplasticity and substantially no phase separation in an aqueous solution comprising at least one polyvalent cation; and (b) at least one acidic liquid solution. The stabilized system can further comprise adding calcium ions to the acidic liquid solution. The amount of calcium ions is preferably from about 10 ppm to about 2000 ppm, and more preferably from about 50 ppm to about 600 ppm.

The acidic liquid solution of the stabilized system comprises proteins selected from at least one of soy, whey, and casein. The acid liquid solution can further comprise a food, cosmetic, or pharmaceutical product to the acidic liquid solution. The food product comprises at least one of fruit and vegetable. The acidic liquid solution can also comprise calcium ions.

Accordingly, it would be desirable to be able to provide a pectin for use in suspending insoluble components in acidic liquid systems that: (1) has shear thinning properties; (2) has shear thinning properties with acceptable mouth-feel; (3) cannot undergo syneresis upon storage or form a separate gel phase in the presence of relatively high levels of calcium; and (4) minimal changes in rheology during long term storage; (5) be effective at low use levels.

DETAILED DESCRIPTION OF THE INVENTION

The present invention is directed to enzymatically blocked-deesterified pectin that displays pseudoplasticity and substantially no phase separation in an aqueous solution comprising at least one polyvalent cation at low use levels.

Pseudoplasticity is a theological behavior most desired for stabilization of particles in aqueous solution. An aqueous solution is characterized as being pseudoplastic if it displays decreasing viscosity with increasing shear rate. This is also referred too as "shear thinning." This behavior is thought to be due to the formation a network structure caused by entanglement of the long chain molecules in solution. Pseudoplastic behavior of pectin is closely related to the relative size of the pectin molecules in solution. Higher molecular weight pectins exhibit this behavior at lower pectin concentrations. One approach toward increasing apparent molecular size is to introduce calcium reactive sites to the high methoxyl pectin molecule by acid deesterification and to add calcium to the solution that forms cross-links between pectin molecules. However, this leads to the formation of gel particles and syneresis and these pectins typically also exhibit thixotropic behavior in solution when calcium is present.

The calcium reactive pectins of this invention have a unique property of pseudoplastic behavior at very low pectin concentrations without gel-contraction or syneresis and are non-thixotropic. In addition, these properties are maintained upon storage at room temperature under acidic conditions.

"Phase separation" refers to the formation of a clear liquid above a suspended bed of particles, often with a clear boundary line. Phase separation could also be referred to as particle sedimentation for the aqueous system containing the pectin of the present invention. Severe phase separation is characterized by clear liquid surrounding the particle bed on the sides as well as the bottom. Phase separation can include, but is not limited to, particle sedimentation and/or gel contraction. "Syneresis" is another term, often used with firm gels and not fluid gels, which is essentially the same as gel contraction, and is yet another representation of phase separation. The test for determining phase separation is described below in the example section labeled "Determination of Particle Sedimentation", which is used to determine phase separation for particle sedimentation.

"Substantially no phase separation" refers to less than 10% of phase separation in the cationic aqueous solution containing the enzymatically blocked-deesterified pectin of the present invention. The phase separation of the enzymatically blocked-deesterified pectin of the present invention is preferably at most about 10%, more preferably at most about 7%, even more preferably about 5%, and at most about 3%.

The enzymatically blocked-deesterified pectin of the present invention is also non-thixotropic in aqueous solutions when reacted with a polyvalent cation. That is, the enzymatically blocked-deesterified pectin of the present invention aids the aqueous solutions to rebuild viscosity or recover very quickly when shear is removed. The rebuild in viscosity after shear is applied is essentially identical to the value for the viscosity before shear is introduced.

In addition, although the enzymatically blocked-deesterified pectin of the present invention does not substantially display phase separation in an aqueous solution comprising at least one polyvalent cation, it does react with polyvalent cations to form molecules of larger apparent molecular size that aids in entanglement for pseudoplasticity at low pectin concentrations. Examples of polyvalent cations preferably include, but are not limited to, aluminum ions, iron ions, manganese ions, calcium ions, and magnesium ions, more preferably calcium ions and magnesium ions, and most preferably calcium ions.

The amount of the polyvalent cation present in the aqueous solution is preferably in the amount of about 10 ppm to about 2,000 ppm, and more preferably about 50 ppm to about 1,000 ppm.

The amount of the calcium ions present in the aqueous solution is preferably in the amount of about 10 ppm to about 2,000 ppm, more preferably about 50 ppm to about 1,000 ppm, and most preferably about 200 ppm to about 600 ppm.

The enzymatically blocked-deesterified pectin of the present invention preferably has a calcium sensitivity (CS) greater than about 200 centipoise (cP) or a calcium fraction (CF) greater than 20, and a Δ degree of esterification (ΔDE) from about 5 to 25%. More preferably, the enzymatically blocked-deesterified pectin has a calcium sensitivity greater than about 200 cP or a calcium sensitive pectin fraction greater than 20, and a Δ degree of esterification from about 7 to 25%. Most preferably, the enzymatically blocked-deesterified pectin has a calcium sensitivity greater than about 200 cP or a calcium sensitive pectin fraction greater than 20, and a Δ degree of esterification from about 8 to 15%.

"Calcium sensitivity (CS)" refers to the property of a pectin product related to an increase in the viscosity of a solution of the pectin product under appropriate conditions.

"Calcium fraction (CF)" refers to a ratio of calcium sensitivities. Methods for determination of CS and CF are described in the Analytical Procedures in the Example Section below.

As discussed above, the term "degree of esterification" is intended to mean the extent to which free carboxylic acid groups contained in the polygalacturonic acid chain of the pectin have been esterified (e.g., by methylation) or in other ways rendered non-acidic (e.g., by amidation). "A degree of esterification ($\Delta DE$)" refers to the difference in the DE between the pectins before enzymatic deesterification as compared to the pectin after enzymatic deesterification. See methods for determination of DE and $\Delta DE$.

In one embodiment of the present invention, the enzymatically blocked-deesterified pectin of the present invention is prepared from a high methoxyl pectin starting material with at least one enzyme. The enzyme may be present upon purification of the pectin, but other embodiments include removal, inctivation or the use of immobilized enzymes. A most preferred embodiment involves the inactivation of the enzyme before precipitation in alcohol.

"Pectin starting material" is intended to mean a pectin product obtained by separation of pectin from a plant material. The pectin starting material can preferably be obtained from citrus peels, apple juices, apple ciders, apple pomade, sugar beets, sunflower heads, vegetables or waste products from plants such as apples, sugar beet, sunflower and citrus fruits, more preferably apples, sugar beets and citrus plants, and most preferably citrus plants such as limes, lemons, grapefruits, and oranges.

The pectin starting material can, for example, be the acid pectin extract after purification or it could be wet pectin cake obtained after treating the acid pectin solution with alcohol. Further, the pectin starting material can, for example, be the dried or partly dried pectin in the pectin cake from precipitation, or it could be the dried, milled pectin powder as normally produced by pectin manufacturers.

As indicated above, the process in accordance with the present invention comprises deesterifying the pectin starting material with at least one enzyme to produce enzymatically blocked-deesterified pectin. The pectin starting material of the present invention preferably has a degree of esterification greater than about 60%, more preferably greater than about 65%, and most preferably greater than about 67%.

In one embodiment of the present invention, if the degree of esterification of the isolated high methoxyl pectin is preferably from about 68 to 72%, then the degree of esterification of the enzymatically blocked-deesterified pectin is preferably from about 45 to 65%, more preferably from about 50 to 62%, and most preferably from about 55 to 59%.

In another embodiment of the present invention, the degree of esterification of the high DE pectin starting material is preferably from about 5 to 25% higher than the enzymatically blocked-deesterified pectin, more preferably from about 5 to 15% higher than the enzymatically blocked-deesterified pectin, and most preferably from about 8 to 15% higher than the enzymatically blocked-deesterified pectin.

The isolated high methoxyl pectin prepared as above is then subjected to a mild controlled deesterifying treatment using a pectin deesterifying enzyme such as pectin methyl esterase isolated from plant materials or organisms capable of producing such enzymes. Examples include but are not limited to the crude enzymes that can contain pectin methyl esterase such as papain, ficin or bromelain. These pectin methyl esterase enzymes deesterify pectins to form blocks of free carboxyl groups.

In one embodiment, a 1 to 2% aqueous solution of the isolated high methoxyl pectin is prepared from dry high DE pectin using appropriate heat and agitation to ensure complete dissolution of the pectin. Then sufficient sodium chloride is added to the preparation to achieve a 1% w/v concentration of sodium chloride based on the original volume of water used in the preparation of the pectin solution. Sodium chloride is known to enhance the activity of pectin deesterifying enzymes. The temperature of this solution is then adjusted to between 20 to 50° C. depending upon the temperature optimum of the deesterifying enzyme used. The pH of the solution is then adjusted to about 5 to 8 using 0.5 M sodium hydroxide (NaOH). Finally, an appropriate amount of the pectin deesterifying enzyme is added to the pectin solution such as any of those produced by the methods described above in order to achieve controlled deesterification.

In the present invention, the ester groups on the pectin are removed in a sequential fashion, preferably by a deesterifying enzyme. Deesterifying enzymes or pectin methyl esterases are pectin enzymes that deesterify pectin to produce free carboxyl groups and free methanol. Deesterifying enzymes in the preferred embodiment deesterify pectins in blockwise manner (sequential fashion). "Blockwise" or "sequential" deesterification occurs when deesterifying enzymes attack pectins either at non-reducing ends or next to free carboxyl groups and then proceed along the pectin molecules by a single-chain mechanism, thereby creating blocks of unesterified galacturonic acid units.

The pectin methyl esterase is extracted from plant tissues selected from, but not limited to, at least one of apples, apricots, avocados, bananas, berries, figs, limes, grapefruits, mandarins, cherries, currants, grapes, mangos, papayas, passion fruits, peaches, pears, pineapple, plums, beans, carrots, cauliflowers, cucumbers, leeks, onions, peas, potatoes, radishes and tomatoes. The enzyme may also be a mixture of more than one pectin methyl esterase from different sources or may also contain other enzymes that act on pectin.

In one preferred embodiment, the enzyme is extracted from papayas. More preferably the enzyme is papain. Most preferably, the enzyme is Colipulin®Liquid product code 5045 manufactured by Gist-Brocades International B.V., Charlotte, N.C. 28224.

The pH of the reaction solution is maintained at about 7 by continuous addition of 0.5 M NaOH. The up-take of NaOH by the solution is used to monitor the progress of the deesterification reaction. Once the deesterification has proceeded to the required degree to produce a pectin in accordance with the invention, the reaction is terminated by the addition of acid to reduce the pH of the solution to 4 or less. The reaction mixture is then heated to approximately 75° C. for 15 minutes to deactivate the enzyme followed by cooling of the mixture. The enzyme treated pectin can then be recovered from the solution by adding an equal volume of 60–80% IPA. The insoluble pectin is collected, pressed and washed with additional volumes of IPA and finally pressed to 30–50% by weight of dry matter.

The enzymatically block-deesterified pectin can further be dried and milled to small particles. Drying of the pectin can be accomplished by any technique in the art (e.g., atmospheric or reduced-pressure ovens) to a moisture content of less than about 50%, preferably less than about 25%. The drying temperature should be maintained below the temperature at which the pectin starts to lose its properties, e.g., color, molecular weight, etc. Any milling technique in the art can be used to mill the pectin product to the desired particle size. It is most preferred that the final product be in dry, powder form, with a moisture content of about 12 wt. % or less. "Dry powder form" is intended to mean that the product be pourable without substantial caking. The preferred final product is in the form of a powder for ease of use.

The process for preparing the deesterified pectin of the present invention can be prepared in a continuous process or a single batch, preferably in a continuous process. In accordance with the present invention, the enzymatically blocked-deesterified pectin can be used in a process for suspending insoluble components in an acidic liquid system. The process includes adding the deesterified pectin that has been deesterified in a sequential pattern to an acidic liquid system.

"Insoluble components" refer to any insoluble particulates such as pulps, essential oils, coloring agents such as natural or otherwise, minerals, botanicals, and pharmaceuticals that have the tendency to phase separate in one or more places in a solution via sedimentation, creaming or other such destabilization mechanisms. The test for phase separation in the context of the present invention is described below in the example section labeled "Determination of Particle Sedimentation" which is a test for phase separation for particle sedimentation.

"Acidic liquid system or acidic aqueous system" herein refers to acidic food, cosmetic, and pharmaceutical products in liquid form which contain a suitable concentration of polyvalent cations or to which polyvalent cations can be added. Examples of liquid food products preferably include, but are not limited to, drinks containing fruits, vegetables, or mixtures thereof, soups, salad dressings, and sauces. The acidic drink can be non-carbonate or carbonate, consumed undiluted or diluted, sweetened or unsweetened, salted or unsalted, with or without alcohol, or combinations thereof.

Examples of liquid acidic cosmetic products include, but are not limited to, perfumes, sun tan lotions, sun screen lotions, body lotions, deodorants, antiperspirants, conditioners and shampoos. Examples of liquid acidic pharmaceutical products include, but are not limited to, cough syrups, liquid forms of headache medicines, liquid forms of decongestants, and liquid forms of anti-inflammatory medicines.

The pH of the acidic liquid system in the process of the present invention is from about 2.0 to about 5, preferably from about 2.5 to about 4.5, and more preferably from about 3 to about 4.

The acidic liquid system can have a solid content from about 0.1% to about 50% by weight, preferably from about 1 to about 30% by weight, and more preferably from about 5 to about 20% by weight.

In one embodiment of the present invention, the acidic liquid system is a beverage drink that can have a solid content from about 0.1% to about 50% by weight, an alcohol content of between from about 0% to about 5% by volume, a salt (NaCl) content of about 0% to 3%, and a sugar content of from about 0.1% to about 15%.

The weight ratio, of the enzymatically blocked-deesterified pectin to the acidic liquid system in the process of the present invention, can be from about 0.0001 to about 0.03, preferably from about 0.0005 to about 0.006, and more preferably from about 0.0015 to about 0.035.

The total amount, of enzymatically blocked-deesterified pectin in the acidic liquid system, can be from about 0.15% to about 0.35% by dry weight, preferably from about 0.05% to about 0.6% by dry weight, and more preferably from about 0.1% to 0.3% by dry weight.

The aqueous system must also contain calcium ions or other polyvalent cations and thus the addition of calcium ions is not optional unless calcium is already present from another ingredient such as a calcium-fortifying agent.

Calcium ions react with the pectin as described in this invention to form a weak gel network of very low but stable viscosity that is pseudoplastic, non-thixotropic and stable at low concentrations. In addition this calcium-pectin solution shows no signs of syneresis. These properties are of particular value to the manufacturer who is seeking to fortify beverages and pharmaceutical products with calcium for nutritional purposes. Calcium levels of about 1000 ppm (i.e., micrograms calcium ion per gram of acidic liquid food) can be achieved without adverse affects on the ability to stabilize particles. This level of calcium addition to a 12 fluid ounce beverage represents a significant amount of the RDA (Recommended Daily Allowance) for calcium for an adult as recommended by the FDA (Food and Drug Administration).

The "stable viscosity" or "stability" that calcium ions provide to the acidic liquid system refers to the maintenance of insoluble components in suspension and the homogeneity of the suspension initially formed. Stability also means that the rheology of the acidic liquid system is stable for a time period of at least one to twelve months or longer.

Calcium ions used in the process of the present invention can be in a solid salt form or solution. Examples of calcium salts include, but are not limited to, calcium chloride, calcium acetate, calcium propionate, calcium oxide, calcium carbonate, calcium citrate, calcium lactate, calcium malonate, calcium gluconate, and, preferably calcium chloride, calcium acetate, calcium propionate, calcium oxide, calcium carbonate, calcium citrate, calcium lactate, calcium malonate, and calcium gluconate, more preferably calcium citrate, calcium lactate, calcium malonate, and calcium gluconate.

The amount of calcium ions in the system can be from about 0.001% to about 0.2% (10 to 2000ppm), preferably from about 0.005% to about 0.1% (50 to 1000 ppm), and more preferably from about 0.02% to about 0.06% (200 to 600 ppm).

The weight ratio of the calcium ions to the enzymatically blocked-deesterified pectin of the present invention can be from about 0.001 to about 10, preferably from about 0.01 to about 1.0, and more preferably from about 0.03 to about 0.30.

The weight ratio of the enzymatically blocked-deesterified pectin, acidic liquid system, and food, cosmetic, or pharmaceutical product in the process of the present invention can be from about 0.0001 to about 0.03, preferably from about 0.0005 to about 0.006, and more preferably from about 0.0015 to about to about 0.035.

When the enzymatically blocked-deesterified pectin of the present invention is added to an acidic liquid, it provides minimal changes in rheology during long term storage. In addition, the pectin of the present invention has shear thinning properties with acceptable mouth-feel. The deesterified pectin of the present invention does not undergo syneresis (form phase separation) upon storage or form a separate gel phase in the presence of relatively high levels of calcium.

The amount of the enzymatically blocked-deesterified pectin in the system of the present invention is from about 0.01% to about 3% by dry weight, preferably from about 0.05 to about 0.6%, and more preferably from about 0.10 to about 0.4%.

Examples of the acidic liquid of the present invention include, but are not limited to, ethanol and water, glycerol and water, and propylene glycol and water. Also in accordance with the present invention, the enzymatically blocked-deesterified pectin can be used in a stabilized acidic liquid system. The stabilized acidic liquid system of the present invention includes an enzymatically blocked-deesterified pectin and an acidic aqueous solution.

"Acidic liquid" herein refers to acidic food, cosmetic, and pharmaceutical products in aqueous form. Examples of liquid food products preferably include, but are not limited to, drinks containing fruits, vegetables, or mixtures thereof, soups, salad dressings and sauces. The acidic drinks can be non-carbonated or carbonate, consumed undiluted or diluted, sweetened or unsweetened, salted or unsalted, with or without alcohol, or combinations thereof.

Examples of liquid acidic cosmetic products include, but are not limited to, perfumes, sun tan lotions, sun screen lotions, body lotions, deodorants, antiperspirants, conditioners and shampoos. Examples of liquid acidic pharmaceutical products include, but are not limited to, cough syrups, liquid forms of headache medicines, liquid forms of decongestants, and liquid forms of anti-inflammatory medicines.

The pH of the acidic aqueous solution of the present invention is from about 2.0 to about 5, preferably from about 2.5 to about 4.5, and more preferably from about 3 to about 4.

The acidic aqueous solution can have a content from about 0.1% to about 50% by volume, preferably from about 1 to about 30% by volume, and more preferably from about 4 to about 18% by volume.

The acidic aqueous solution in the stabilized acidic liquid system is from about 2.5 to about 5, preferably from about 2.8 to about 4.5, and more preferably from about 3 to about 5.

In addition, the system can further include a food, cosmetic or pharmaceutical product. Alternatively, the system can further include (1) calcium ions and (2) a food, cosmetic or pharmaceutical product.

The weight ratio of the enzymatically deesterified pectin and the calcium ions in the stabilized acidic liquid system is from about 0.001 to about 0.2, preferably from about 0.005 to about 0.01, and more preferably from about 0.02 to about 0.06.

Without further elaboration, it is believed that one skilled in the art can, using the preceding description, utilize the present invention to its fullest extent.

The following preferred specific embodiments are, therefore, to be construed as merely illustrative, and not limitative of the remainder of the disclosure in any way whatsoever.

EXAMPLES

Examples 1–6 provided below, illustrate different physical properties of the deesterified pectin known in the art and the deesterified pectin of the present invention, as well as processes of preparing and using the same. Also illustrate below are analytical procedures for determining physical properties of the deesterified pectins.

Analytycal Procedures
Method for Measuring Calcium Sensitivity

Calcium sensitivity can preferably be calculated by measuring calcium sensitivity (CS) of pectin in a solution with gum. Specifically, calcium salt and pectin are mixed at low pH where there is no strong setting of calcium ions and pectin. Then the reaction between pectin and calcium ions is started by addition of sodium acetate/acetic acid buffer. The apparatus used in this calculation are: (1) plate magnetic stirrer (IKA MAG EOA 9); (2) magnetic stirrer (JK IKA-Combimag REO); (3) 50×110 mm viscosity glass (Holm & Halby); (4) 25 ml dispenser; (5) 5 ml automatic pipette; (6) Brookfield viscosimeter LVT; (7) pH-meter; (8) technical balance; (9) analytical balance; (10) 42mm TRIKA magnets; and (11) cooling bath (thermostatically controlled at 25° C.)

The reagents used in this calculation are (1) 1.000 M HCl; (2) 1 M acetate buffer at pH 4.75 (68.04g/l of 500 mM $CH_3COONa$ and $3H_2O$, and 28.6 ml/l of 500 MM $CH_3COOH$ (100%)); and (3) 250 mM calcium chloride (36.7550g/l $CaCl_2$ and $2H_2O$). Ion exchanged water with a conductivity below 1.0 uS/cm must be used in all solutions. The pectin solution contains 400 g pectin solution with 2.4 g pure gum (0.6% sol.). If the testing sample is not 100% gum (pure gum), the sample is corrected using the following formula (A=the gum % of the sample):

(0.6×400)/A=g sample with A % gum for 400 g solution.

The procedure for the calculating the calcium sensitivity is as follows: (1) weigh out the pectin with adjusted sugar percentage to 3 decimals; (2) disperse the pectin into 240 ml boiling ion-exchanged water in a high shear mixer; (3) pour the solution into a tared beaker with magnet; (4) pour additional 100 ml ion exchanged water into the mixer and add to the solution; (5) cool the pectin solution to about 25° C.; (6) adjust the pectin solution to a pH of 1.5 with 1 M HCl; (7) weigh the solution to 400 g; (8) weigh out 145 g±1 g pectin solution in a viscosity glass; (9) put a TRIKA magnet in the glass; (10) add 5 ml 250 mM Ca++ solution to the pectin solution while stirring with the plate magnetic stirrer at step (9). Stir for 2 min; (11) add 25 ml 1 M acetate buffer with dispenser to the glass while stirring with a magnetic stirrer (JK IKA-Combimag REO) (the pH is about 4.2); (12) stir for an additional 2 minutes as described in step (10); (13) remove the magnet and let the solution rest at 25° C. until next day; and (14) measure calcium sensitivity as viscosity in cP with Brookfield LVT viscosimeter at 60 rpm/25° C. (use the thermostatically controlled water bath).

Method for Determining Degree of Esterification

The degree of esterification of the pectin can be determined as presented below. Weigh 5 g of the pectin sample to the nearest 0.1 mg and transfer to a suitable beaker. Stir for 10 minutes with a mixture of 5 ml of 37% fuming hydrochloric acid and 100 ml of 60% IPA. Transfer to a fitted glass filter tube (30 to 60 ml capacity) and wash with 6×15 ml portions of the fuming HCl-60% IPA mixture, followed by 60% IPA until the filtrate is free of chlorides. Finally, wash with 20 ml of 100% IPA, dry for 2.5 hours in an oven at 105° C., cool in a desiccator and weigh the sample. Transfer exactly 1/10 of the total net weight of the dried sample (representing 0.5 g of the original unwashed sample) to a 250 ml conical flask and moisten the sample with 2 ml of IPA. Add 100 ml of recently boiled and cooled distilled water, stopper and swirl occasionally until a complete solution is formed. Add 5 drops of phenolphthalein, titrate with 0.1 N sodium hydroxide and record the results as the initial titre ($V_1$).

Add exactly 20 ml of 0.5 N sodium hydroxide, stopper, shake vigorously and let stand for 15 minutes. Add exactly 20 ml of 0.5 N hydrochloric acid and shake until the pink colour disappears. After adding 3 drops of phenolphthalein, titrate with 0.1 N sodium hydroxide to a faint pink colour which persists after vigorous shaking; record this value as the saponification titre ($V_2$).

Quantitatively transfer the contents of the conical flask into a 500-ml distillation flask fitted with a Kjeldahl trap and a water-cooled condenser, the delivery tube of which extends well beneath the surface of a mixture of 150 ml of carbon dioxide-free water and 20 ml of 0.1 N hydrochloric acid in a receiving flask. To the distillation flask add 20 ml of a 1-in-10 sodium hydroxide solution, seal the connections, and then begin heating carefully to avoid excessive foaming. Continue heating until 80–120 ml of distillate has been collected. Add a few drops of methyl red to the receiving flask, and titrate the excess acid with 0.1 N sodium hydroxide, recording the volume (ml) required as "S". Perform a blank determination on 20 ml of 0.1 N hydrochloric acid, and record the volume (ml) required as "B". Record the amide titre (B-S) as $V_3$.

The degree of esterification (as % of total carboxyl groups) is calculated by the formula:

$$DE = 100 \times \frac{V_2}{V_1 + V_2 + V_3}$$

Method for Determining A Calcium Sensitivity and Calcium Fraction (CF)

A change in the calcium sensitivity ($\Delta CS$) of a pectin sample can be determined as presented below.

An aqueous solution of the pectin is prepared in distilled water and its pH adjusted to 1.5 with 1 M HCl. The concentration used should be around 0.60%. 145 g portions of this pectin solution are measured into viscosity glasses. 5 ml of a solution containing 250 mM calcium chloride is added to the 145 g pectin solution to give a final concentration of 8.3 mM calcium. With efficient stirring with a magnetic stirrer, 25 ml of an acetate buffer containing 1 M of acetate ions and a pH of 4.75, is added to the pectin solution to bring the pH to 4.2.

The magnet is removed, and the glass is left at room temperature (25° C.) until the next day, when the viscosity is measured at 25° C. with a Brookfield viscometer.

While the method is most suitable for pectin samples having a viscosity not higher than 100, viscosity up to 200 Brookfield units can be measured with good reproducibility. Pectin samples with higher viscosity tend to gel, resulting in less reproducible results. The method, however, gives a fair indication of the relative calcium sensitivity of samples.

When the viscosity of the same pectin sample is measured without the addition of calcium chloride but diluted with distilled water, the $\Delta CS$ value of the pectin is calculated by subtracting the measured viscosity value for the calcium free solution from the measured viscosity value for the calcium containing solution. CF is determined by dividing the measured viscosity value for the calcium free solution into the viscosity value for the calcium containing solution.

Determination of Particle Sedimentation

Particle sedimentation is evaluated by placing samples of commercially available juice based beverages which contain insoluble particles to which the test pectins are added, into 15 cm high screw capped tubes which have outside diameters (OD) of 16 nm. Examples of such beverages include Frutopia Strawberry Passion, Libby Juicy Juice, Ocean Spray Orange Juice, Ocean Spray Ruby Red Grapefruit Juice, Snapple Island Cocktail, and Tropicana Twister.

Solutions of the test pectins (2% w/w) are prepared and added to the beverages to achieve a final concentration of 0.1 wt. %. The tubes are allowed to stand refrigerated at 3° C. for four weeks. At that point, the height of the clear liquid column above the particle suspension is measured. A percent sedimentation is calculated by dividing the height of the clear layer ($H_C$) by the total height ($H_T$) of the liquid in the tube (clear layer+pulp suspended) as shown below:

$(H_C/H_T) \times 100$

Examples of Pectin Production

Examples 1 and 3 provided below illustrate the preparation of known deesterified pectin of the present invention.

Example 1

Production of a 60% DE Block Deesterified Pectin

A block deesterified pectin (BD Pectin) is made from unconcentrated rapid-set pectin juice.

Unconcentrated rapid-set pectin juice can be made as follows:

10 kg of dried lemon peel (Argentina) is added to a 500 liter (working volume) stirred tank reactor. 0.8 liter of nitric acid (62 wt. % HNO3, Olin Corp., Chemicals Group, Norwalk, Conn. 06856 USA) is further added to the reactor to reach a pH of 0.9 to 1.2. Pectin is extracted from the lemon peel by heating the mixture with slight agitation to 70° C. for 3 hours. The extraction mixture is then filtered using vacuum filtration followed by a vacuum polishing filtration using Celite (Celite Corp., c/. World Minerals Inc. Lompoc, Calif. 93438 USA). The filtrate is evaporated using a wiped film evaporator to increase the pectin concentration in solution to approximately 1.6% w/w. The pH of the clear filtrate is adjusted to 4.0 by the addition of a sodium carbonate solution (Na2CO3, CERAC, Inc. Milwaukee, Wis. 53201 1178 USA.

The DE for the rapid-set pectin starting material at this point is approximately 73%. The temperature is adjusted to 45° C. and pH is adjusted to 5.5 with $NH_3$. An enzyme that contains pectin methylesterase (Collupuling® Liquid product code 5045 manufactured by Gist-Brocades International B.V., Charlotte, N.C. 28224) is added to the juice. The pH is held constant by titration with 2% $NH_3$.

The enzyme is inactivated by lowering pH to 2.5 with $HNO_3$ and the temperature is adjusted to 80° C. and held for 10 minutes. After cooling the juice is precipitated 1:3 in 80% 2-propanol and washed in 60% 2-propanol. The block-deesterified (BD) pectin is precipitated in 80/20 IPA/water, pressed to remove excess IPA water and dried.

Analysis of Pectin shows % DE=59.8%; GA=84.9; and MW=87000.

Example 2

Production of a 60% DE Block Deesterified Pectin of the Present Invention

The process for producing the BD pectin of the present invention is similar to that found in the procedures of Example 1 except an enzyme step is added after evaporation of the pectin juice and prior to precipitation with IPA. The enzyme step requires the addition of a stirred bio-reactor stage to the pectin process. In the bio-reactor stage, the temperature of the pectin juice is cooled to 30° C. or less to minimize pectin degradation following neutralization. Next, the pectin juice is adjusted to pH value from 5 to 7 with sodium bicarbonate with stirring. Pectin esterase is then added to deesterify the pectin. The pH is maintained for several hours during the deesterification by the addition of a base such as sodium hydroxide, sodium bicarbonate, sodium carbonate, or ammonium hydroxide. At the end of the reaction, the mixture is adjusted to a pH of less than 4 and heated to at least 85° C. to inactivate the enzyme. The pectin solution is then cooled to a temperature normally used for precipitation. The block-deesterified (BD) pectin is precipitated in 80/20 IPA/water, pressed to remove excess IPA water and dried.

Examples 3–6 provided below illustrate that the deesterified pectin of the present invention provides suspension of insoluble components in acidic aqueous solution.

Example 3

Production of a 55% DE Block Deesterified Pectin

Prepare a 1% pectin solution by dissolving 50 grams of BB Rapid Set Pectin 70.5% DE (from Hercules Copenhagen Pectin, Lille Skensved, Denmark, DK-4623) in 5 liters of deionized water at 75° C. to 80° C. and stirring until pectin is completely dissolved. 50 grams of ammonium chloride is added to the pectin solution and the solution is cooled to 30 to 40° C. The pH is adjusted to 7.0 with dilute aqueious sodium hydroxide. 2.5 ml of pectin methylesterase (Collupulin® Liquid product code 5045 manufactured by Gist-Brocades International B.V., Charlotte, N.C. 28224) is added to the solution. The solution is titrated with 1 N ammonium hydroxide and the pH is maintained between 6.8 and 7.2 until the DE of the pectin reaches 55%. The amount of 1 N ammonium hydroxide used was 35.3 ml. The pH of the solution is adjusted to pH4 with dilute HCl and the solution is heated to 85° C. for 2 to 5 minutes to inactivate the enzyme. The pectin solution is cooled to room temperature and precipitated with 80/20 IPA water solution. The pectin is coolected by filtering through fine nylon mesh cloth and the material is pressed to remove excess IPA/water. The block-deesterified (BD) pectin is pre-dried in a hood for 2–3 hours and then dried in a vacuum oven for 16–20 hours under vacuum at 50° C. The dried BD Pectin is milled through a 1 mm pore size screen on a Brinkman High Speed Ultracentrifugal Electric Grinder type 2M-1.

Examples 4–7 provided below illustrate that the deesterified pectin of the present invention provides suspension of insoluble components in acidic aqueous solution.

Example 4

Pulp Suspension in Orange Juice Drinks 473 ml of orange juice, Tropicana Pure Premium Orange Juice from Tropicana Products, Inc., Fla. 34206 is decanted into a one-liter beaker. Then 47.3 ml of a 1.5% pectin solution (as prepared in Example 2 above) is added to the orange drink with stirring on a lightning stirrer for 5 minutes.

1.135 g of calcium citrate powder (calcium citrate tetrahydrate CA142 food grade manufactured by Spectrum Quality Products, Inc.) is added slowly to the orange drink while mixing. The mixing is continued for another 10 minutes and the pH is measured.

The treated drink is pasteurized at 85° C. for 15 minutes. The hot drink is poured back into the original bottle and capped. The treated bottle is cooled to room temperature and mixed by inverting the bottle several times.

The sample is observed for a one month period for settling of pulp and compared to a control sample that is prepared without adding pectin. After two weeks, the sample with the pectin of the present invention is determined to be stabilized if no significant settling has occured.

Example 5

Pulp Suspension in Lemonade Juice Drinks

The materials required for this experiment are: 47.3 ml of 1.5% solution of BD pectin as prepared in Example 2; a 16-ounce bottle of Ocean Spray Pink Lemonade manufactured by Ocean Spray Cranberry Inc. Lakeville Middlemore, Me. 02349; calcium citrate (in powder form) (calcium citrate tetrahydrate CA142 food grade manufactured by Spectrum Quality Products, Inc.); water bath at 70° C.; and lightning stirrer.

The bottle of Ocean Spray Pink lemonade is poured into a 1 liter beaker. 47.3 ml of 1.5% of pectin solution is added to the lemonade and mixed with a lightning stirrer for 5 minutes. 1.1353 grams of calcium citrate is then added to the lemonade and mixed for an additional 10 minutes. The treated lemonade is pasteurized at 85° C. for 15 minutes and placed back in its original bottle. The settling is compared to an untreated control.

The results illustrate that the pectin/calcium treated sample does not settle even after 6 months storage at room temperature (as compared to untreated Ocean Spray Pink lemonade bottles which settled in less than 24 hours at room temperature or 4° C.).

Example 6

Settling Rate of Particles at 30% and 100% Orange Juice with Pectin The materials required for this example are: one 16 oz can (355 ml) of Tropicana, Season's Best, Pulp Free, frozen orange juice concentrate (manufactured by Tropicana Products Inc. Bradenton, Fla. 34206); BD Pectin (60% DE) as prepared in Example 2; 500ml Pyrex Graduated cylinders with stoppers; Water Bath at 90° C.; pH Meter; and 10% Sugar Water.

The amount of ingredients used in this example is provided in Table 1 below:

TABLE 1

| Amount of Ingredients used for Orange Juice (ml): | | |
|---|---|---|
|  | 30% Juice | 100% Juice |
| Concentrate | 106 | 355 |
| 1% Pectin Sol. (0.15%) | 212.85 | 212.85 |
| 10% Water | 1099.65 (Sugar Water) | 851.15 Deionized Water |
| Total | 1419 | 1419 |

The measured amount of pectin solution is added to a suitable container. Juice concentrate and sugar water/or deionized water is added to the pectin solution. The mixture is initially mixed with a rubber spatula by scrapping the pectin solution from the sides and bottom of the container, then the mixture is stirred by lightening stir at medium speed for 5 minutes. 0.2% Calcium Citrate is added to the mixture while stirring at medium speed for an additional 10 minutes.

The juice is titrated with 50% citric acid to pH 3.6. Pasteurization is then conducted at 85° C. for 5 minutes. The hot juice is poured into a 500 ml cylinder to the 500 ml mark, and the cylinder is immediately capped with a stopper to keep the juice sterile. The next day, the juice is mixed by slowly inverting the cylinder.

The result shows that the settling rate of pulp particles in both 30 and 100 percent juice is up to 60 times slower in the treated samples as compared to the control which contains no added pectin.

Example 7

Mineral Suspension in a Nutritional Beverage

The Nutritional Beverage used for this experiment is Ultra Slim Fast (manufactured by Slim Fast Foods Co. West Palm Beach Fla. 33402). BD Pectin is added to the Slim Fast and is compared with Control with no added pectin. Samples are examined over a length of time to determinine mineral suspension stability. This is done by Hot Treatment and Cold Treatment.

Hot Treatment refers to adding pectin in hot Slim Fast at 70–80° C. Cold Treatment refers to adding pectin in Slim Fast at ambient temperature.

Four samples of Slim Fast are used in this experiment. The hot treatment includes two samples (Samples 1 and 2). Sample 1 is Ultra Slim Fast drink (manufactured by Slim Fast Foods Co. West Palm Beach Fla. 33402). Sample 2 is Ultra Slim Fast drink and blocked-deesterified (BD) pectin of the present invention (as prepared in Example 2).

The cold treatment includes two samples (Samples 3 and 4). Sample 3 is Ultra Slim Fast drink (manufactured by Slim Fast Foods Co. West Palm Beach Fla. 33402). Sample 4 is Ultra Slim Fast drink and BD pectin of the present invention (as prepared in Example 2).

The procedure for performing this experiment are as follows: 1.5% BD pectin solution is prepared by dissolving pectin in deionized water at 70–75° C. Pour 1 part of pectin solution and 9 parts of Ultra Slim Fast drink while mixing with a Silverson Mixer at 5,000 rpm to make a final pectin concentration of 0.15%. The pH of the mixture is checked to be at pH 3. The control is then prepared with 1 part of deionized water and 9 parts of Nutritional Beverage. The mineral suspension stability of the pectin stabilizer is compared with a Control Sample over a length of time.

The results for Hot and Cold Treatments with pectins of the present invention and Control Samples after 48 hours are shown in Table 2 below.

TABLE 2

| Hot Treatment | Cold Treatment |
| --- | --- |
| Control Sample 1: Sedimentation of the mineral is observed at the bottom of the container | Control Sample 3: Sediment observed is less than that observed with the Hot Treatment. |
| Control Sample 2 (Pectin): Mineral remains suspended without any settling. | Control Sample 4 (Pectin): Mineral remains suspended. |

The preceding examples can be repeated with similar success by substituting the generically and specifically described constituents and/or operating conditions of this invention for those used in the preceding examples. From the foregoing descriptions, one skilled in the art can easily ascertain the essential characteristics of this invention, and without departing from the spirit and scope thereof, can make various changes and modifications of the invention to adapt to various usages and conditions.

What is claimed is:

1. An enzymatically blocked-deesterified pectin displaying pseudoplasticity and substantially no phase separation in aqueous solution comprising at least one polyvalent cation, wherein the enzymatically blocked-deesterified pectin has
   (1) a degree of esterification from about 45 to 62%, and
   (2) a calcium sensitivity greater than about 200 cP or a calcium fraction greater than 20; and
   wherein the amount of the enzymatically blocked-deesterified pectin in the aqueous solution is from about 0.05% to about 0.6%.

2. The enzymatically blocked-deesterified pectin of claim 1, wherein the amount of polyvalent ion is from about 10 ppm to about 2,000 ppm.

3. The enzymatically blocked-deesterified pectin of claim 2, wherein the polyvalent is selected from one of aluminum ions, iron ions, manganese ions, calcium ions, and magnesium ions.

4. The enzymatically blocked-deesterified pectin of claim 3, wherein the polyvalent is calcium ion, and wherein the amount of calcium ion is from about 10 ppm to about 2,000 ppm.

5. The enzymatically blocked-deesterified pectin of claim 4, wherein the amount of calcium ion is from about 200 ppm to about 600 ppm.

6. The enzymatically blocked-deesterified pectin of claim 4, wherein the calcium ions react with the enzymatically blocked-deesterified pectin forming a gel network of stable viscosity.

7. The enzymatically blocked-deesterified pectin of claim 6, wherein the weight ratio of the calcium ions to the enzymatically blocked-deesterified pectin is from about 0.001 to about 10.

8. The enzymatically blocked-deesterified pectin of claim 1, wherein the amount of phase separation in the aqueous solution is at most about 10%.

9. The enzymatically blocked-deesterified pectin of claim 8, wherein the amount of phase separation in the aqueous solution is at most about 5%.

10. The enzymatically blocked-deesterified pectin of claim 9, wherein the amount of phase separation in the aqueous solution is at most about 3%.

11. The enzymatically blocked-deesterified pectin of claim 1 having a degree of esterification from about 50 to 62%.

12. The enzymatically blocked-deesterified pectin of claim 11 having a degree of esterification from about 55 to 59%.

13. The enzymatically blocked-deesterified pectin of claim 11 having a Δ degree of esterification from about 5 to 25%.

14. The enzymatically blocked-deesterified pectin of claim 13 having a Δ degree of esterification from about 8 to 15%.

15. The enzymatically blocked-deesterified pectin of claim 11 prepared by treating the isolated high methoxyl pectin with an enzyme, wherein the enzyme is extracted from plant tissues selected from at least one of apples, apricots, avocados, bananas, berries, limes, grapefruits, mandarins, cherries, currants, grapes, mangos, papayas, passion fruits, peaches, pears, plums, beans, carrots, cauliflowers, cucumbers, leeks, onions, peas, potatoes, radishes and tomatoes.

16. The enzymatically blocked-deesterified pectin of claim 15 having degree of esterification from about 45 to 62% when the degree of esterification of the isolated high methoxyl pectin is from about 68 to 72%.

17. The enzymatically blocked-deesterified pectin of claim 1 prepared by treating isolated high methoxyl pectin with enzyme.

18. The enzymatically blocked-deesterified pectin of claim 17, wherein the enzyme is extracted from plant tissues selected from at least one of apples, apricots, avocados, bananas, berries, limes, grapefruits, mandarins, cherries, currants, grapes, mangos, papayas, passion fruits, peaches, pears, plums, beans, carrots, cauliflowers, cucumbers, leeks, onions, peas, potatoes, radishes and tomatoes.

19. The enzymatically blocked-deesterified pectin of claim 17, wherein the enzyme is papain.

20. The enzymatically blocked-deesterified pectin of claim 17 having degree of esterification from about 45 to 62% when the degree of esterification of the isolated high methoxyl pectin is from about 68 to 72%.

21. The enzymatically blocked-deesterified pectin of claim 20 having degree of esterification from about 55 to 59% when the degree of esterification of the isolated high methoxyl pectin is from about 68 to 72%.

22. The enzymatically blocked-deesterified pectin of claim 17, wherein the isolated high methoxyl pectin has a degree of esterification greater than about 60%.

23. The enzymatically blocked-deesterified pectin of claim 22, wherein the isolated high methoxyl pectin has a degree of esterification greater than about 67%.

24. The enzymatically blocked-deesterified pectin of claim 17, wherein the isolated high methoxyl pectin is in an aqueous form or powder form.

25. The enzymatically blocked-deesterified pectin of claim 17, wherein the isolated high methoxyl pectin is obtained from at least one of citrus peels, apple juices, apple ciders, apple pomade, sugar beets, sunflower heads, vegetables or waste products from plants selected from at least one of apples, sugar beet, sunflower and citrus fruits.

26. The enzymatically blocked-deesterified pectin of claim 25, wherein the isolated high methoxyl pectin is obtained from at least one of limes, lemons, grapefruits, tangerines and oranges.

27. The enzymatically blocked-deesterified pectin of claim 1, wherein the amount of the enzymatically blocked-deesterified pectin in the aqueous solution is from about 0.1% to about 0.3%.

28. The enzymatically blocked-deesterified pectin of claim 1, wherein the amount of the enzymatically blocked-deesterified pectin in the aqueous solution is from about 0.15% to about 0.35%.

29. A process for producing an enzymatically blocked-deesterified pectin which comprises treating at least one isolated high methoxyl pectin with at least one deesterifying enzyme, wherein the enzymatically blocked-deesterified pectin displays pseudoplasticity and substantially no phase separation in aqueous solution comprising at least one polyvalent cation,
   wherein the enzymatically blocked-deesterified pectin has
      (1) a degree of esterification from about 45 to 62%, and
      (2) a calcium sensitivity greater than about 200 cP or a calcium fraction greater than 20; and
   wherein the amount of the enzymatically blocked-deesterified pectin in the aqueous solution is from about 0.05% to about 0.6%.

30. The process for producing an enzymatically blocked-deesterified pectin of claim 29, wherein the amount of polyvalent ion is from about 10 ppm to about 2,000 ppm.

31. The process for producing an enzymatically blocked-deesterified pectin of claim 30, wherein the polyvalent is selected from one of aluminum ions, iron ions, manganese ions, calcium ions, and magnesium ions.

32. The process for producing an enzymatically blocked-deesterified pectin of claim 31, wherein the polyvalent is calcium ion, and wherein the amount of calcium ion is from about 10 ppm to about 2,000 ppm.

33. The process for producing an enzymatically blocked-deesterified pectin of claim 32, wherein the amount of calcium ion is from about 200 ppm to about 600 ppm.

34. The process for producing an enzymatically blocked-deesterified pectin of claim 32, wherein the calcium ions react with the enzymatically blocked-deesterified pectin forming a gel network of stable viscosity.

35. The process for producing an enzymatically blocked-deesterified pectin of claim 34, wherein the weight ratio of the calcium ions to the enzymatically blocked-deesterified pectin is from about 0.001 to about 10.

36. The process for producing an enzymatically blocked-deesterified pectin of claim 29, wherein the amount of phase separation in the aqueous solution is at most about 10%.

37. The process for producing an enzymatically blocked-deesterified pectin of claim 36, wherein the amount of phase separation in the aqueous solution is at most about 5%.

38. The process for producing an enzymatically blocked-deesterified pectin of claim 37, wherein the amount of phase separation in the aqueous solution is at most about 3%.

39. The process for producing an enzymatically blocked-deesterified pectin of claim 29, wherein the enzyme is extracted from plant tissues selected from at least one of apples, apricots, avocados, bananas, berries, limes, grapefruits, mandarins, cherries, currants, grapes, mangos, papayas, passion fruits, peaches, pears, plums, beans, carrots, cauliflowers, cucumbers, leeks, onions, peas, potatoes, radishes and tomatoes.

40. The process for producing an enzymatically blocked-deesterified pectin of claim 29, wherein the enzyme is papain.

41. The process for producing an enzymatically blocked-deesterified pectin of claim 29, wherein the isolated high methoxyl pectin is obtained from at least one of citrus peels, apple juices, apple ciders, apple pomade, sugar beets, sunflower heads, vegetables or waste products from plants selected from at least one of apples, sugar beet, sunflower and citrus fruits.

42. The process for producing an enzymatically blocked-deesterified pectin of claim 41, wherein the isolated high methoxyl pectin is obtained from at least one of limes, lemons, grapefruits, tangerines and oranges.

43. The process for producing an enzymatically blocked-deesterified pectin of claim 29, wherein the isolated high methoxyl pectin is in an aqueous form or powder form.

44. The process for producing an enzymatically blocked-deesterified pectin of claim 29, wherein the isolated high methoxyl pectin has a degree of esterification greater than about 60%.

45. The process for producing an enzymatically blocked-deesterified pectin of claim 44, wherein the isolated high methoxyl pectin has a degree of esterification greater than about 67%.

46. The process for producing an enzymatically blocked-deesterified pectin of claim 29, wherein if the degree of esterification of the isolated high methoxyl pectin is from about 68 to 72%, the degree of esterification of the enzymatically blocked-deesterified pectin is from about 45 to 62%.

47. The process for producing an enzymatically blocked-deesterified pectin of claim 46, wherein if the degree of esterification of the isolated high methoxyl pectin is from about 68 to 72%, the degree of esterification of the enzymatically blocked-deesterified pectin is from about 55 to 59%.

48. The process for producing an enzymatically blocked-deesterified pectin of claim 29, wherein the isolated high methoxyl pectin is obtained from at least one of citrus peels, apple juices, apple ciders, apple pomade, sugar beets, sunflower heads, vegetables or waste products from plants selected from at least one of apples, sugar beet, sunflower and citrus fruits.

49. The process for producing an enzymatically blocked-deesterified pectin of claim 48, wherein the isolated high methoxyl pectin is obtained from at least one of limes, lemons, grapefruits, tangerines and oranges.

50. The process for producing an enzymatically blocked-deesterified pectin of claim 49, wherein the isolated high methoxyl pectin is in an aqueous form or powder form.

51. The process for producing an enzymatically blocked-deesterified pectin of claim 50, wherein the enzymatically blocked-deesterified pectin has a Δ degree of esterification from about 5 to 25%.

52. The process for producing an enzymatically blocked-deesterified pectin of claim 51, wherein the enzymatically blocked-deesterified pectin has a Δ degree of esterification from about 8 to 15%.

53. The process for producing an enzymatically blocked-deesterified pectin of claim 52, wherein the enzymatically blocked-deesterified pectin has a degree of esterification from about 50 to 62%.

54. The process for producing an enzymatically blocked-deesterified pectin of claim 29, wherein the amount of the enzymatically blocked-deesterified pectin in the aqueous solution is from about 0.1% to about 0.3%.

55. The process for producing an enzymatically blocked-deesterified pectin of claim 29, wherein the amount of the enzymatically blocked-deesterified pectin in the aqueous solution is from about 0.15% to about 0.35%.

56. A process for suspending insoluble components in an acidic liquid system which comprises adding enzymatically blocked-deesterified pectin that has been deesterified with enzyme to acidic liquid system, wherein the enzymatically blocked-deesterified pectin displays pseudoplasticity and substantially no phase separation in aqueous solution comprising at least one polyvalent cation,
  wherein the enzymatically blocked-deesterified pectin has
    (1) a degree of esterification from about 45 to 62%, and
    (2) a calcium sensitivity greater than about 200 cP or a calcium fraction greater than 20; and
  wherein the amount of the enzymatically blocked-deesterified pectin in the aqueous solution is from about 0.05% to about 0.60%.

57. The process of claim 56, wherein the amount of polyvalent ion is from about 10 ppm to about 2,000 ppm.

58. The process of claim 57, wherein the polyvalent is selected from one of aluminum ions, iron ions, manganese ions, calcium ions, and magnesium ions.

59. The process of claim 58, wherein the polyvalent is calcium ion, and wherein the amount of calcium ion is from about 10 ppm to about 2,000 ppm.

60. The process of claim 59, wherein the amount of calcium ion is from about 200 ppm to about 600 ppm.

61. The process of claim 59, wherein the calcium ions react with the enzymatically blocked-deesterified pectin forming a gel network of stable viscosity.

62. The process of claim 61, wherein the weight ratio of the calcium ions to the enzymatically blocked-deesterified pectin is from about 0.001 to about 10.

63. The process of claim 56, wherein the amount of phase separation in the aqueous solution is at most about 10%.

64. The process of claim 63, wherein the amount of phase separation in the aqueous solution is at most about 5%.

65. The process of claim 64, wherein the amount of phase separation in the aqueous solution is at most about 3%.

66. The process of claim 56, wherein the enzymatically blocked-deesterified pectin has a Δ degree of esterification from about 5 to 25%.

67. The process of claim 66, further comprises adding calcium ions to the acidic liquid system.

68. The process of claim 67, wherein the amount of calcium ions is from about 10 ppm to about 2000 ppm.

69. The process of claim 68, wherein the amount of calcium ions is from about 50 ppm to about 1000 ppm.

70. The process of claim 69, wherein the amount of calcium ions is from about 200 ppm to about 600 ppm.

71. The process of claim 67, wherein the weight ratio of the enzymatically deesterified pectin and the calcium ions is from about 0.001 to about 0.2.

72. The process of claim 71, wherein the weight ratio of the enzymatically deesterified pectin and the calcium ions is from about 0.005 to about 0.01.

73. The process of claim 72, wherein the weight ratio of the enzymatically deesterified pectin and the calcium ions is from about 0.02 to about 0.06.

74. The process of claim 76, wherein the protein is at least one of soy, whey, and casein.

75. The process of claim 66, wherein the acidic liquid system comprises protein.

76. The process of claim 67, further comprises adding a food, cosmetic, or pharmaceutical product to the acidic liquid system, wherein the food product comprises at least one of fruit and vegetable.

77. The process of claim 56, wherein the acidic liquid system comprises calcium ions.

78. The process of claim 77, wherein the amount of calcium ions is from about 10 ppm to about 2000 ppm.

79. The process of claim 78, wherein the amount of calcium ions is from about 50 ppm to about 1000 ppm.

80. The process of claim 79, wherein the amount of calcium ions is from about 200 ppm to about 600 ppm.

81. The process of claim 77, wherein the weight ratio of the enzymatically deesterified pectin and the calcium ions is from about 0.005 to about 0.01.

82. The process of claim 81, wherein the weight ratio of the enzymatically deesterified pectin and the calcium ions is from about 0.02 to about 0.06.

83. The process of claim 82, wherein the acidic liquid system comprises protein.

84. The process of claim 77, wherein the acidic liquid system comprises protein, wherein the protein is at least one of soy, whey, and casein.

85. The process of claim 77, further comprises adding a food, cosmetic, or pharmaceutical product to the acidic liquid system.

86. The process of claim 85, wherein the food product comprises at least one of fruit and vegetable.

87. The process of claim 56, wherein the amount of the enzymatically esterified pectin is from about 0.01% to about 3.0% by dry weight in the final acidic liquid system.

88. The process of claim 87, wherein the amount of the enzymatically esterified pectin is from about 0.05% to about 0.6% by dry weight in the final acidic liquid system.

89. The process of claim 88, wherein the amount of the enzymatically esterified pectin is from about 0.15% to about 0.35% by dry weight in the final acidic liquid system.

90. The process of claim 56, wherein the pH of the acidic liquid system is from about 2.0 to about 5.

91. The process of claim 90, wherein the pH of the acidic liquid system is from about 2.5 to about 4.5.

92. The process of claim 91, wherein the pH of the acidic liquid system is from about 3 to about 4.

93. The process of claim 56, wherein the enzymatically blocked-deesterified pectin has a Δ degree of esterification from about 5 to 25%.

94. The process of claim 56, wherein the enzymatically blocked-deesterified pectin is prepared by deesterifying an isolated high methoxyl pectin with an enzyme, wherein the enzyme is extracted from plant tissues selected from at least one of apples, apricots, avocados, bananas, berries, limes, grapefruits, mandarins, cherries, currants, grapes, mangos, papayas, passion fruits, peaches, pears, plums, beans, carrots, cauliflowers, cucumbers, leeks, onions, peas, potatoes, radishes and tomatoes.

95. The process of claim 56, wherein the enzymatically blocked-deesterified pectin is prepared by deesterifying an isolated high methoxyl pectin with an enzyme, wherein the enzyme is papain.

96. The process of claim 56, wherein the enzymatically blocked-deesterified pectin has a degree of esterification from about 50 to 62%.

97. The process of claim 96, wherein the enzymatically blocked-deesterified pectin has a degree of esterification from about 55 to 59%.

98. The process claim 56, wherein the amount of the enzymatically blocked-deesterified pectin in the aqueous solution is from about 0.1% to about 0.3%.

99. The process claim 56, wherein the amount of the enzymatically blocked-deesterified pectin in the aqueous solution is from about 0.15% to about 0.35%.

100. A stabilized acidic liquid system comprising (a) at least one enzymatically blocked-deesterified pectin that displays pseudoplasticity and substantially no phase separation in aqueous solution comprising at least one polyvalent cation; and (b) at least one acidic liquid solution,
    wherein the enzymatically blocked-deesterified pectin has
        (1) a degree of esterification from about 45 to 62%, and
        (2) a calcium sensitivity greater than about 200 cP or a calcium fraction greater than 20; and
    wherein the amount of the enzymatically blocked-deesterified pectin in the aqueous solution is from about 0.05% to about 0.6%.

101. The stabilized acidic liquid system of claim 100, wherein the amount of polyvalent ion is from about 10 ppm to about 2,000 ppm.

102. The stabilized acidic liquid system of claim 101, wherein the polyvalent is selected from one of aluminum ions, iron ions, manganese ions, calcium ions, and magnesium ions.

103. The stabilized acidic liquid system of claim 102, wherein the polyvalent is calcium ion, and wherein the amount of calcium ion is from about 10 ppm to about 2,000 ppm.

104. The stabilized acidic liquid system of claim 103, wherein the amount of calcium ion is from about 200 ppm to about 600 ppm.

105. The stabilized acidic liquid system of claim 103, wherein the calcium ions react with the enzymatically blocked-deesterified pectin forming a gel network of stable viscosity.

106. The stabilized acidic liquid system of claim 105, wherein the weight ratio of the calcium ions to the enzymatically blocked-deesterified pectin is from about 0.001 to about 10.

107. The stabilized acidic liquid system of claim 100, wherein the amount of phase separation in the aqueous solution is at most about 10%.

108. The stabilized acidic liquid system of claim 107, wherein the amount of phase separation in the aqueous solution is at most about 5%.

109. The stabilized acidic liquid system of claim 108, wherein the amount of phase separation in the aqueous solution is at most about 3%.

110. The stabilized acidic liquid system of claim 100, further comprises adding calcium ions to the acidic liquid solution.

111. The stabilized acidic liquid system of claim 110, wherein the amount of calcium ions is from about 10 ppm to about 2000 ppm.

112. The stabilized acidic liquid system of claim 111, wherein the amount of calcium ions is from about 50 ppm to about 600 ppm.

113. The stabilized acidic liquid system of claim 110, wherein the weight ratio of the enzymatically deesterified pectin and the calcium ions is from about 0.001 to about 0.2.

114. The stabilized acidic liquid system of claim 113, wherein the weight ratio of the enzymatically deesterified pectin and the calcium ions is from about 0.005 to about 0.01.

115. The stabilized acidic liquid system of claim 114, wherein the weight ratio of the enzymatically deesterified pectin and the calcium ions is from about 0.02 to about 0.06.

116. The stabilized acidic liquid system of claim 110, wherein the acidic liquid solution comprises protein.

117. The stabilized acidic liquid system of claim 116, wherein the protein is at least one of soy, whey, and casein.

118. The stabilized acidic liquid system of claim 110, further comprises adding a food, cosmetic, or pharmaceutical product to the acidic liquid solution.

119. The stabilized acidic liquid system of claim 118, wherein the food product comprises at least one of fruit and vegetable.

120. The stabilized acidic liquid system of claim 100, wherein the acidic liquid solution comprises calcium ions.

121. The stabilized acidic liquid system of claim 120, wherein the amount of calcium ions is from about 10 ppm to about 2000 ppm.

122. The stabilized acidic liquid system of claim 121, wherein the weight ratio of the enzymatically deesterified pectin and the calcium ions is from about 0.001 to about 0.2.

123. The stabilized acidic liquid system of claim 120, wherein the weight ratio of the enzymatically deesterified pectin and the calcium ions is from about 0.005 to about 0.01.

124. The stabilized acidic liquid system of claim 123, wherein the weight ratio of the enzymatically deesterified pectin and the calcium ions is from about 0.02 to about 0.06.

125. The stabilized acidic liquid system of claim 124, wherein the amount of calcium ions is from about 50 ppm to about 1000 ppm.

126. The stabilized acidic liquid system of claim 120, wherein the acidic liquid solution comprises protein, wherein the protein is at least one of soy, whey, and casein.

127. The stabilized acidic liquid system of claim 120, further comprises adding a food, cosmetic, or pharmaceutical product to the acidic liquid solution.

128. The stabilized acidic liquid system of claim 127, wherein the food product comprises at least one of fruit and vegetable.

129. The stabilized acidic liquid system of claim 100, wherein the amount of the enzymatically esterified pectin is from about 0.01% to about 3.0% by dry weight in the final acidic liquid solution.

130. The stabilized acidic liquid system of claim 129, wherein the amount of the enzymatically esterified pectin is from about 0.05% to about 0.6% by dry weight in the final acidic liquid solution.

131. The stabilized acidic liquid system of claim 100, wherein the pH of the acidic liquid solution is from about 2.5 to about 5.

132. The stabilized acidic liquid system of claim 100, wherein the enzymatically-blocked-deesterified pectin has a $\Delta$ degree of esterification from about 5 to 25%.

133. The stabilized acidic liquid system claim 100, wherein the enzymatically blocked-deesterified pectin is prepared by deesterifying an isolated high methoxyl pectin with an enzyme, wherein the enzyme is extracted from plant tissues selected from at least one of apples, apricots, avocados, bananas, berries, limes, grapefruits, mandarins, cherries, currants, grapes, mangos, papayas, passion fruits, peaches, pears, plums, beans, carrots, cauliflowers, cucumbers, leeks, onions, peas, potatoes, radishes and tomatoes.

134. The stabilized acidic liquid system of claim 100, wherein the enzymatically blocked-deesterified pectin is prepared by deesterifying an isolated high methoxyl pectin with an enzyme, wherein the enzyme is papain.

135. The stabilized acidic liquid system of claim 100, wherein the enzymatically blocked-deesterified pectin has a degree of esterification from about 50 to 62%.

136. The stabilized acidic liquid system of claim 100, wherein the amount of the enzymatically blocked-deesterified pectin in the aqueous solution is from about 0.1% to about 0.3%.

137. The stabilized acidic liquid system of claim 100, wherein the amount of the enzymatically blocked-deesterified pectin in the aqueous solution is from about 0.15% to about 0.35%.

* * * * *

US006428837C1

(12) EX PARTE REEXAMINATION CERTIFICATE (5870th)

United States Patent
Luzlo et al.

(10) Number: US 6,428,837 C1
(45) Certificate Issued: *Aug. 21, 2007

(54) DEESTERIFIED PECTINS, PROCESSES FOR PRODUCING SUCH PECTINS, AND STABILIZED ACIDIC LIQUID SYSTEMS COMPRISING THE SAME

(75) Inventors: Gary Luzlo, Newark, DE (US); Susan C. Forman, Newark, DE (US); Timothy C. Gerrish, Kennett Square, PA (US)

(73) Assignee: CP Kelco APS, Wilmington, DE (US)

Reexamination Request:
No. 90/006,834, Oct. 28, 2003

Reexamination Certificate for:
Patent No.: 6,428,837
Issued: Aug. 6, 2002
Appl. No.: 09/589,887
Filed: Jun. 9, 2000

Filed Aug. 30, 2006 DED, O.G. citation Nov. 21, 2006 VOC1312 No. 3, Claims disclaimed 1 through 137.

(*) Notice: This patent is subject to a terminal disclaimer.

(51) Int. Cl.
*A23L 2/00* (2006.01)
*A23L 2/02* (2006.01)
*A23L 1/0524* (2006.01)

(52) U.S. Cl. ............. 426/599; 426/50; 426/51; 426/577; 426/590

(58) Field of Classification Search .............. None
See application file for complete search history.

(56) References Cited

U.S. PATENT DOCUMENTS

| | | | |
|---|---|---|---|
| 4,529,613 A | 7/1985 | Mezzino et al. |
| 5,286,511 A | 2/1994 | Klavons et al. |
| 5,639,494 A | 6/1997 | Grassin et al. |
| 5,648,112 A | 7/1997 | Yang et al. |
| 5,690,975 A | 11/1997 | Akahoshi et al. |
| 5,707,847 A | 1/1998 | Christgau et al. |
| 5,780,081 A | 7/1998 | Jacobson et al. |
| 5,866,190 A | 2/1999 | Barey |
| 6,143,346 A | 11/2000 | Glahn |
| 6,159,503 A | 12/2000 | Glahn |
| 6,207,194 B1 | 3/2001 | Glahn |
| 6,221,419 B1 | 4/2001 | Gerrish |
| 6,528,085 B2 | 3/2003 | Madsen |
| 6,699,977 B1 | 3/2004 | Gerrish et al. |
| 2003/0162746 A1 | 8/2003 | Madsen |

FOREIGN PATENT DOCUMENTS

| | | |
|---|---|---|
| EP | 664300 | 7/1995 |
| GB | 1474990 | 5/1977 |
| GB | 9817805.6 | 8/1998 |
| GB | 2342921 | 4/2000 |
| WO | 89/12648 | 12/1989 |
| WO | 91/15517 | 10/1991 |
| WO | 94/25575 | 11/1994 |
| WO | 97/03574 | 2/1997 |
| WO | 00/08952 | 2/2000 |
| WO | WO 00/08952 | 2/2000 |
| WO | 00/15830 | 3/2000 |
| WO | 01/96590 | 12/2001 |

OTHER PUBLICATIONS

English Language Abstract of JP 8–112059, May 7, 1996.
Kravtchenko et al., Food Macromolecules and colloids; proceedings of a conference, Dijon, Mar. 1994, 349–355, "Colloidal Stability and Sedimentation of Pectin–Stabilized Acid Milk Drinks".
Kravtchenko et al., "Characterization of Industrial High Methoxy Pectins", pp. 26–35.
Parker et al , "Effects of the Addition of High Methoxy Pectin on the Rheology and Colloidal Stability of Acid Milk Drinks", pp. 307–312, 1994.
Glahn, FIA–Japan, PEG/JK (dai–24a)–Apr. 4, 1995, pp. 1–6, Fig 1 & pp. 1–4, & 1–4 & 1–3.
Glahn et al., Gums and Stabilisers for the Food Industry 8, edited by Phillips et al,, IIRL Press, Properties and Food Uses of Pectin Fractions, pp. 393–402.
Glahn, Prog. Fd. Nutr. Sci., vol. 6, pp. 171–177, 1982, "Hydrocolloid Stabilization of Protein Suspensions at Low pH".
Speiser et al., Journal of the American Chemical Society, vol. 68 Feb. 1946, pp. 117–133, "Effect of Molecular Association and Charge Distribution of the Gelation of Pectin".
Speiser et al , "Effect of Molecular Weight and Method of Deesterification on the Gelling Behavior of Pectins", 1946, pp. 287–293.
Kohn et al, Die Nahrung, vol. 29 (1985)1, pp. 75–85.
Markovic et al., Experientia (Base1)40(8), 1984, pp. 842–843.
Industrial Gums—Polysaccharides and Their Derivatives, Third Edition, Ed. by Whistler et al, Academic Press, New York, 1993, Chapter 10, pp. 257–291.
Matsuura et al., Agric. Biol. Chem., 51(6), 1675–1677, 1987, "Limit to the Deesterification of Citrus Pectin by Citrus Pectinesterase".
Hill et la., Food Technology, vol. 3, Mar. 1949, pp. 90–93, "Enzyme–Demethylated Pectinates and Their Gelation".
Jarvis, Plant, Cell and Environment (1984) 7, 153–164, "Structure and Properties of Pectin Gels in Plant Cell Walls".

(Continued)

*Primary Examiner*—Jerry D Johnson

(57) ABSTRACT

Enzymatically blocked-deesterified pectins that display pseudoplasticity and substantially no phase separation in aqueous solutions comprising at least one polyvalent cation, and processes for producing the same. Enzymatically blocked-deesterified pectins prepared by deesterifying isolated high methoxyl pectins with enzymes. Processes for suspending particulates using enzymatically blocked-deesterified pectins enzymatically blocked-deesterified pectins prepared by deesterifying isolated high methoxyl pectins with enzymes. Compositions and stabilized aqueous systems containing enzymatically blocked-deesterified pectins prepared by deesterifying isolated high methoxyl pectins with enzymes.

OTHER PUBLICATIONS

Solms et al., Helv. Chim. Acta, 38, pp. 321–329, "Uber den Mechanismus der enzymatischen Verseifung von Pektinstoffen".

Kohn et al, Collect. Checz. Chem. Commun., 33, pp. 264–269, 1968, "Distribution of Free Carboxyl Groups in the Pectin Molecule After Treatment, With Pectin Esterase".

Rolin, "Calcium Sensitivity of High Ester Citrus Pectins", 1994, Oxford University Press, edited by Glyn O. Phillips et al., pp. 413–422.

Pilnik and Voragen. "The Significance of Endogenous and Exogenous Pectic Enzymes in Fruit and Vegetable Processing." *Food Enzymology*, Ed.: P.F.Fox; Elsevier; (1991); pp. 303–337).

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–137 are now disclaimed.

* * * * *